US012484864B2

(12) United States Patent
Mithani et al.

(10) Patent No.: US 12,484,864 B2
(45) Date of Patent: Dec. 2, 2025

(54) SCATTER RADIATION PROTECTION DEVICE

(71) Applicant: O&M Halyard, Inc., Mechanicsville, VA (US)

(72) Inventors: Namita A. Mithani, Alpharetta, GA (US); Emma Amick, Davidson, NC (US); Caroline Aurelio, Orland Park, IL (US); Frank Ketchum, Alpharetta, GA (US); Monica Behara, Milton, GA (US); Careniena Opem, Falls Church, VA (US)

(73) Assignee: O&M Halyard, Inc., Glen Allen, VA (US)

( * ) Notice: Subject to any disclaimer, the term of this patent is extended or adjusted under 35 U.S.C. 154(b) by 470 days.

(21) Appl. No.: 18/075,826

(22) Filed: Dec. 6, 2022

(65) Prior Publication Data

US 2023/0172568 A1 Jun. 8, 2023

Related U.S. Application Data

(60) Provisional application No. 63/286,206, filed on Dec. 6, 2021.

(51) Int. Cl.
*A61B 6/10* (2006.01)
*G21F 1/12* (2006.01)

(52) U.S. Cl.
CPC .............. *A61B 6/107* (2013.01); *G21F 1/125* (2013.01)

(58) Field of Classification Search
CPC ................................ A61B 6/107; G21F 1/125
See application file for complete search history.

(56) References Cited

U.S. PATENT DOCUMENTS

| | | | |
|---|---|---|---|
| 1,907,523 | A | 5/1933 | Egressi et al. |
| 4,062,518 | A | 12/1977 | Stivender et al. |
| 7,294,845 | B2 | 11/2007 | Ballsieper |
| 7,391,042 | B2 | 6/2008 | Goldstein |
| 7,465,947 | B2 | 12/2008 | Magram |
| 7,608,847 | B2 | 10/2009 | Rees |
| 7,667,214 | B2 | 2/2010 | Cadwalader et al. |
| 8,113,713 | B2 | 2/2012 | Belson et al. |

(Continued)

FOREIGN PATENT DOCUMENTS

| | | | |
|---|---|---|---|
| CA | 3072454 | A1 | 11/2019 |
| DE | 10325567 | B | 6/1958 |

(Continued)

OTHER PUBLICATIONS

Fetterly et al., "Effective Use of Radiation Shields to Minimize Operator Dose During Invasive Cardiology Procedures", JACC: Cardiovascular Interventions, vol. 4, No. 10, 2011 8 pages.

(Continued)

*Primary Examiner* — Nicole M Ippolito
(74) *Attorney, Agent, or Firm* — Dority & Manning, P.A.

(57) ABSTRACT

A scatter radiation protection device is provided. The scatter radiation protection device includes a barrier that is movable in an x-direction, a y-direction, and a z direction; a skirt that is movable in an x-direction; and a sliding track having an upper surface and a lower surface. The barrier and the skirt are configured for connection to the sliding track, and the barrier and the skirt provide for at least 0.5 millimeters of lead (mmPb) equivalence.

19 Claims, 11 Drawing Sheets

(56) References Cited

U.S. PATENT DOCUMENTS

| | | | | |
|---|---|---|---|---|
| 9,820,702 | B2 | 11/2017 | Osherov et al. | |
| 10,932,976 | B2 | 3/2021 | Conner et al. | |
| 11,207,039 | B2 | 12/2021 | Foster et al. | |
| 2012/0241652 | A1 | 9/2012 | Jeschke | |
| 2020/0211725 | A1* | 7/2020 | Yifat | G21F 1/125 |
| 2020/0352528 | A1 | 11/2020 | Foster et al. | |
| 2023/0058574 | A1* | 2/2023 | Lemer | A61B 6/107 |

FOREIGN PATENT DOCUMENTS

| | | | |
|---|---|---|---|
| EP | 2509506 | B1 | 2/2017 |
| EP | 2126928 | B1 | 9/2018 |
| WO | WO 2011/085273 | A1 | 7/2011 |
| WO | WO 2015/018240 | A1 | 2/2015 |

OTHER PUBLICATIONS

International Search Report and Written Opinion for PCT/US2022/051944, dated Mar. 21, 2023, 13 pages.
Akram et al., "Radiation Exposure of Medical Imaging", NCBI Bookshelf, 2021, 9 pages.
Annis, Faye, "Scatter Drapes Used In Interventional Radiology Procedures", 3 pages https://blog.universalmedicalinc.com/author/faye/.
Azimuddin et al., "An ergonomic assessment of operating table and surgical stool heights for seated otolaryngology procedures", Allergy Rhinol, vol. 8, No. 3, Oct. 2017, 7 pages.
Chung et al., "Radiation protection effect of mobile shield barrier for the medical personnel during endoscopic retrograde cholangiopancreatography: a quasi-experimental prospective study", BMJ Open, vol. 9, 2019, 6 pages.
Fast facts on U.S. hospitals, 2021: AHA. American Hospital Association. https://www.aha.org/statistics/fast-facts-us-hospitals. Accessed Dec. 10, 2021.
Gill et al., "Shoulder range of movement in the general population: age and gender stratified normative data using a community-based cohort", BMC Musculoskeletal Disorders, 2020, 9 pages.
Griffing, George T., "Doctor, You Should Now Measure Abdominal Height", The Medscape Journal of Medicine, vol. 10, 2008, 3 pages.
Heron et al., "Radiation protection of medical staff", European Journal of Radiology, vol. 76, 2010, 4 pages.
Kahn et al., "Indicators of abdominal size relative to height associated with sex, age, socioeconomic position and ancestry among US adults", PLOS One, Mar. 1, 2017, 18 pages.
Kim et al., "A study on the measurement of wrist motion range using the iPhone 4 gyroscope application", Ann Plast Surg., Aug. 2014, 1 page.
Mahesh, Mahadevappa, "Flouroscopy: Patient Radiation Exposure Issues", The AAPM/RSNA Physics Tutorial for Residents, vol. 21, No., Jul.-Aug. 2001, 13 pages.
Mavig for Siemens—Radiation protective drape for Radial Access. https://www.mavig.com/siemens/products/ceiling_suspended_shields/radiation-protective-drape-for-radial-access/. Accessed Sep. 28, 2021, 2 pages.
McCaffrey, et al., "Radiation attenuation by lead and nonlead materials used in radiation shielding garments", Med,. Phys. vol. 34, Feb. 2007, 8 pages.
Mettler, Jr., et al., "Patient Exposure from Radiologic and Nuclear Medicine Procedures in the United States: Procedure vol. and Effective Dose for the Period 2006-2016", Radiology, vol. 295, No. 2, May 2020, 10 pages.
Schueler, Beth A., PhD, "Operator Shielding: How and Why", Techniques in Vascular and Interventional Radiology, vol. 13, 2010, 5 pages.
Tunakova et al., "Hybrid knitted fabric for electromagnetic radiation shielding", Journal of Engineered Fibers and Fabrics, vol. 15, 2020, 9 pages.
Vasen et al., "Functional Range of Motion of the Elbow", J. Hand Surg, vol. 20A, 1995, 5 pages.
Rampart M1128. Rampart IC. https://www.rampartic.com/rampart-m1128. Accessed Sep. 19, 2021, 4 pages.
Introduction to Radiographic Equipment, Radiology Key, https://radiologykey.com/introduction-to-radiographic-equipment, 7 pages.
X-ray lead glass. Lead Glass Pro. https://leadglasspro.com/products/x-ray-lead-glass. Accessed Dec. 11, 2021, 1 page.

* cited by examiner

SCATTER RADIATION PROTECTION DEVICE

RELATED APPLICATIONS

The present application claims priority to U.S. Provisional Application Ser. No. 63/286,206, filed on Dec. 6, 2021, which is incorporated herein in its entirety by reference thereto.

FIELD

The present invention relates to a protection device to decrease exposure to scatter radiation during imaging-based medical procedures.

BACKGROUND

Fluoroscopies provide real-time imaging during medical procedures by utilizing ionizing radiation directed at the patient. However, the primary radiation emanating from a radiation source can scatter when the beam interacts with the patient's body tissue. This scatter radiation is deflected from the tissue and may be directed towards medical personnel standing nearby, while remnant radiation travels towards the image receptor of an imaging device. Consistent exposure to this type of radiation puts medical personnel at risk for both short-term side and long-term side effects. Short-term side effects include nausea, fatigue, weakness, destruction of bone marrow, or GI syndrome. Long-term exposure to scatter radiation puts medical personnel at risk for serious ailments including cancer, cataracts, and sperm or egg damage.

Exposure can be reduced by limiting the amount of fluoroscopy time, increasing the distance between staff and the beam, and utilizing physical barriers to block and absorb the scatter. To decrease exposure of scatter radiation to medical personnel and others, numerous types of protective equipment exist. Some of the protective equipment that medical personnel may wear can include lead aprons, lead goggles, thyroid shields, lead caps, and lead gloves. However, due to inconsistency in training, lack of availability of these garments, the heavy weight of aprons, and decreased finger mobility with gloves, these devices have limited compliance from medical personnel. Scatter drapes placed on the patient are also utilized to protect from scatter radiation in certain procedures. Since these devices are not applicable for every body type or surgery entry point, they are not always used. Large shields and barriers made of lead acrylic or glass may also be wheeled into the operating room or lowered from the ceiling. Due to their high cost, limited mobility, and lack of compatibility with various access points, they are not always utilized. Another chief complaint from users is the difficulty of set-up, leading to overall lack of compliance with these protective devices. Further, despite the emphasis placed on radiation safety by hospital staff, many physicians and other medical personnel tend to prioritize their patients' health concerns over their own. Medical personnel will frequently ignore warnings when they know that they are near their exposure limit so that they will be able to perform procedures. Therefore, a need exists for a solution to reduce exposure to scatter radiation that is easily usable for procedures across medical specialties.

SUMMARY

Objects and advantages of the present disclosure will be set forth in part in the following description, or may be obvious from the description, or may be learned through practice of the present disclosure.

The present disclosure provides for a scatter radiation protection device. The scatter radiation protection device includes a barrier, wherein the barrier is movable in an x-direction, a y-direction, and a z direction; a skirt, wherein the skirt is movable in an x-direction; and a sliding track having an upper surface and a lower surface. The barrier and the skirt are configured for connection to the sliding track, and the barrier and the skirt each provide for at least 0.5 millimeters of lead (mmPb) equivalence.

In one embodiment, the barrier can include a first barrier and a second barrier.

In another embodiment, the barrier can include a cutout section to define an opening.

In yet another embodiment, the skirt can include a first portion and a second portion.

In still another embodiment, the barrier can include transparent or translucent material. Further, the barrier can include leaded glass or leaded acrylic.

In one more embodiment, the skirt can include lead.

In an additional embodiment, the skirt is further movable in the y-direction.

In one embodiment, the sliding track can define a groove around a perimeter of the sliding track. Further, the groove can be located on an upper surface of the sliding track.

In another embodiment, the barrier and the skirt can be connected to the sliding track via hinge. Further, the hinge can be slidable, rotatable, or a combination thereof. Additionally, the device can include a barrier support, where the barrier can be connected to the barrier support via an additional hinge. Further, the additional hinge can be slidable, rotatable, or a combination thereof.

In addition, the barrier can be slidable in the y-direction by a height H via the third hinge. Further, the height, H, can range from about 1 centimeter to about 75 centimeters.

In yet another embodiment, the scatter radiation protection device can include an attachment means configured to connect the scatter radiation protection device to a table. Further, the barrier and the skirt can both be slidable around an entire perimeter of the table.

Moreover, the scatter radiation protection device can exhibit greater than 95% reduction in scatter radiation exposure compared to when the scatter radiation protection device is not used.

These and other features, aspects, and advantages of the present disclosure will become better understood with reference to the following description and appended claims. The accompanying drawings, which are incorporated in and constitute a part of this specification, illustrate embodiments of the present disclosure and, together with the description, serve to explain the principles of the present disclosure.

BRIEF DESCRIPTION OF THE FIGURES

A full and enabling disclosure of the present disclosure, including the best mode thereof, directed to one of ordinary skill in the art, is set forth in the specification, which makes reference to the appended figures, in which.

DETAILED DESCRIPTION

Figure 1A:
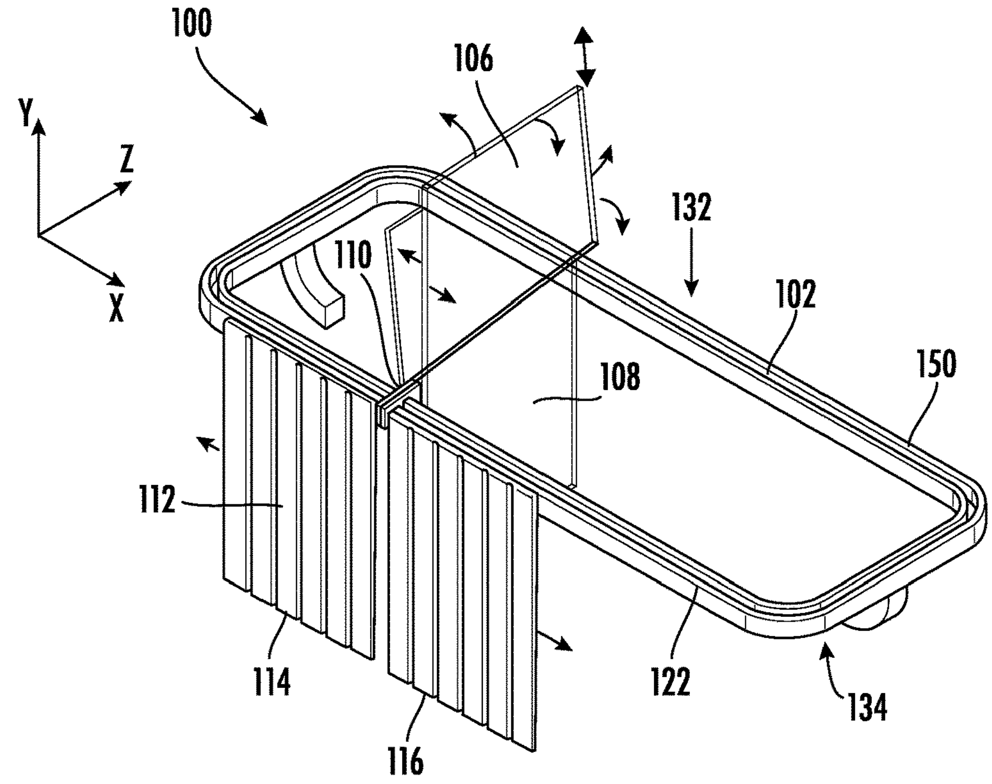
FIG. 1A illustrates a perspective view of one embodiment of the device of the present disclosure.

Reference will now be made in detail to one or more embodiments of the present disclosure, examples of the present disclosure, examples of which are illustrated in the drawings. Each example and embodiment is provided by way of explanation of the disclosure and is not meant as a limitation of the disclosure. For example, features illustrated or described as part of one embodiment may be used with another embodiment to yield still a further embodiment. It is intended that the disclosure include these and other modifications and variations as coming within the scope and spirit of the disclosure.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present disclosure. For example, if ranges of "from about 20% to about 80%" and "from about 30% to about 70%" are described, a range of "from about 20% to about 70%" or a range of "from about 30% to about 80%" are also contemplated by the present disclosure.

Generally speaking, the present disclosure is directed to a scatter radiation protection device. The scatter radiation protection device includes a barrier, wherein the barrier is movable in an x-direction, a y-direction, and a z direction; a skirt, wherein the skirt is movable in an x-direction; and a sliding track having an upper surface and a lower surface. The barrier and the skirt are configured for connection to the sliding track, and the barrier and the skirt each provide for at least 0.5 millimeters of lead (mmPb) equivalence. The present inventors have found that the features of the present disclosure improve user compliance due to its portability, ease of use, and comfort for medical personnel without sacrificing the effectiveness of reducing exposure to scatter radiation. The configurability of the device of the present disclosure is also a benefit. For instance, some specialties, such as urology, medical personnel will only need scatter radiation protection in one place. Other specialties, like interventional cardiology or orthopedics, may operate at different locations on the body and will thus need a device that is easily configurable and has features that allow for protection at various locations along a patient body where treatment or imaging may occur. In addition, there are usually one to two physicians, nurses, attendings, students, and anesthesiologists present during procedures, all of whom need protection at different places in the room. These factors inform the design of the configurable device of the present disclosure, which can be used for any surgery. In addition, configurability also extends to the patient, and the device of the present disclosure is compatible for use with a wide variety of body shapes and sizes.

The scatter radiation protection device, which can be table-mounted, can include a first barrier and a second barrier formed from leaded glass or leaded acrylic and a leaded skirt, which are attached to a sliding track that can completely surround a perimeter of an operating table. The first barrier and the second barrier can adjust vertically in the y-direction to allow the device to be compatible with patients of many different sizes. Further, both the barriers and/or the skirt can provide at least 0.5 mmPb equivalence, such as at least about 0.75 mmPb equivalence, such as at least about 1 mmPb equivalence, such as at least about 1.25 mmPb equivalence, such as at least about 1.5 mmPb equivalence, such as at least about 1.6 mmPb equivalence, ensuring adequate protection for the upper and lower body of medical personnel who may be exposed to scatter radiation emanating from the patient during a radiation-based procedure.

Referring now to FIGS. 1A-10, the various features of the device contemplated by the present disclosure will be described in more detail. Turning first to FIGS. 1A through 1D, various perspective views of various configurations of the scatter radiation protection device 100 of the present disclosure are shown. First, in FIG. 1A, the scatter radiation protection device 100 includes a sliding track 102. The scatter radiation protection device can also include a first barrier 106, a second barrier 108, and a skirt 112. The first barrier 106 and the second barrier 108 can be formed from leaded glass, leaded acrylic, or any other suitable material that can attenuate radiation. Further, the first barrier 106 and the second barrier 108 can be transparent or translucent such that medical personnel can see through the first barrier 106 and the second barrier 108 to perform medical procedures or imaging on a patient. The skirt 112 may have a first portion 114 and a second portion 116. The skirt 112 can be formed of any suitable material 118, such as any suitable woven or non-woven material, and can include lead 120 to provide for protection from scatter radiation. The first barrier 106, the second barrier 108, and the skirt 112 are movable along the sliding track 102 via hinges 110, which may fit into grooves 122 along an upper surface 132 of the sliding track 102. In some embodiments, the first barrier 106 and first portion 114 of the skirt 112 may be attached to the sliding track 102 via a first hinge 110A, while the second barrier 108 and the second portion 116 of the skirt 112 may be attached to the sliding track 102 via a second hinge 1106. However, it should be understood that each component (e.g., the first barrier 106, the second barrier 108, the first portion 114 of the skirt 112, and/or second portion 116 of the skirt 112) may be attached to the sliding track 102 via their own individual hinges 110.

As shown in FIGS. 1A-1D, the first barrier 106 and the second barrier 108 can be positioned above or below the sliding track 102 and are rotatable about the x-axis, the y-axis, and the z-axis. Further, the first barrier 106 and the second barrier 108 are slidable along the x-axis and the y-axis via the sliding track 102 around its entire perimeter 150. As can be seen in FIGS. 1A-1D, the first barrier 106 and/or the second barrier 108 can be positioned above an upper surface 132 of the sliding track 102 or below a lower surface 134 of the sliding track 102. Meanwhile, the skirt 112, including first portion 114 and second portion 114, is slidable along the x-axis and the y-axis via the sliding track 102 around its entire perimeter 150. Further, the skirt 102 can be positioned below the lower surface 134 of the sliding track.

The hinges 110 and/or 110B used to attach the first barrier 106 and the second barrier 108 to the sliding track 102 can be in the form of a locking hinge that can rotate 180 degrees in the x, y, and z directions to allow for the first barrier 106 and the second barrier 108 to be configured into any desired position to protect medical personnel.

Figure 1B:
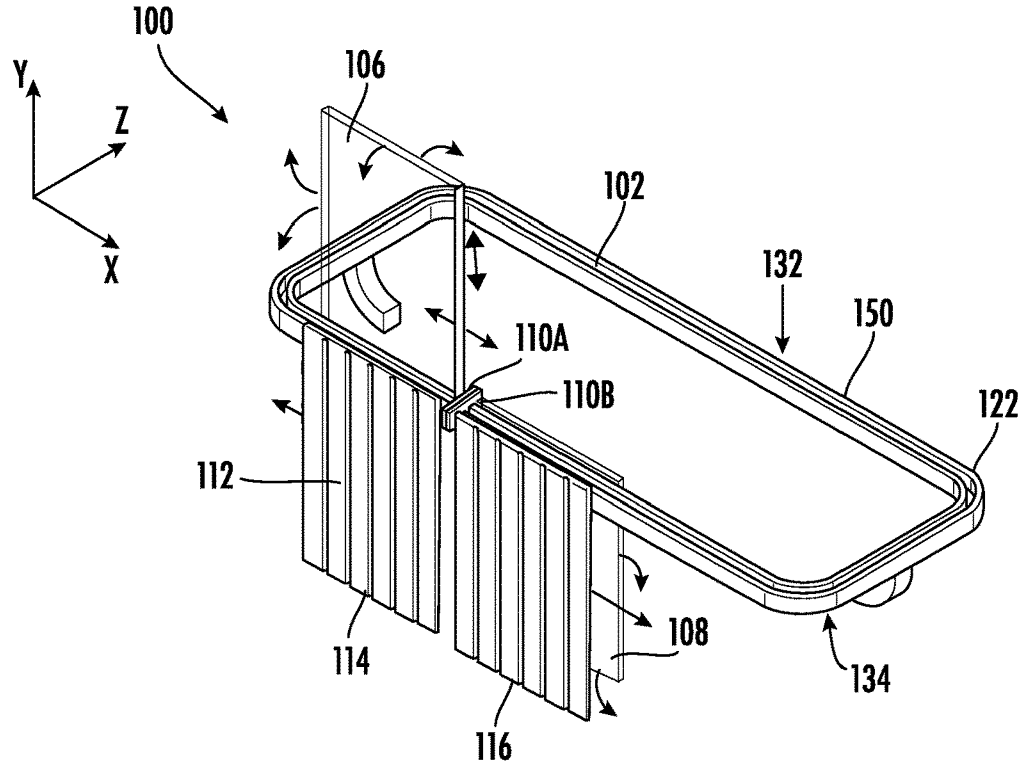
FIG. 1B illustrates another perspective view of one embodiment of the device of the present disclosure.
Figure 1C:
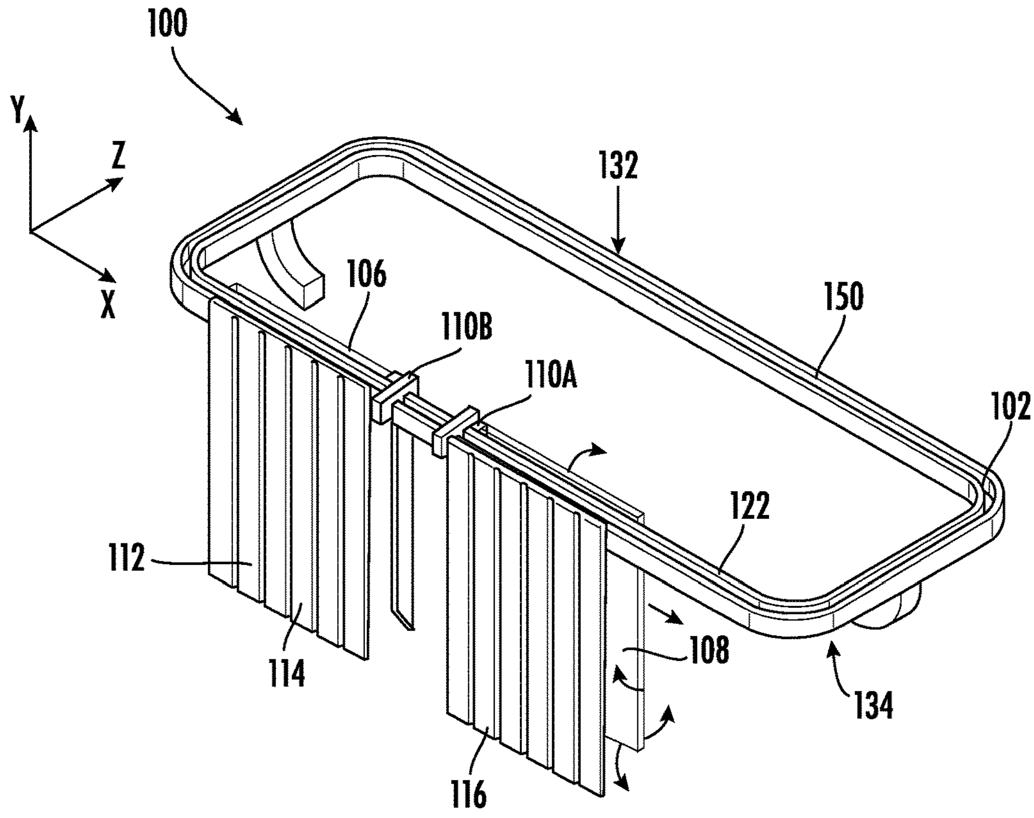
FIG. 1C illustrates yet another perspective view of one embodiment of the device of the present disclosure.
Figure 1D:
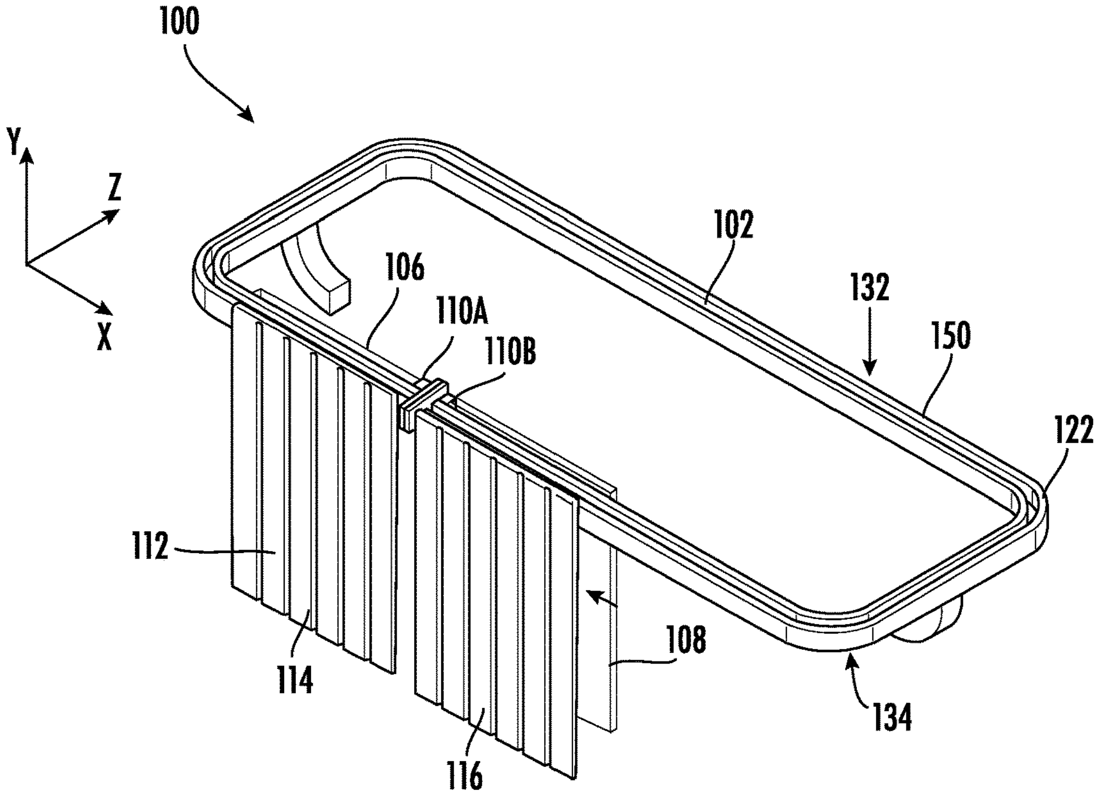
FIG. 1D illustrates still another perspective view of one embodiment of the device of the present disclosure.

In FIG. 1A, the first barrier 106 and the second barrier 108 are aligned with the z-axis, with the first barrier 106 being positioned above the second barrier 108, while the first portion 114 and second portion 116 of the table skirt are aligned with the x-axis. In FIG. 1B, the first barrier 106 and the second barrier 108 are aligned with the x-axis, with the first barrier 106 being positioned above an upper surface 132 of the sliding track 102 and the second barrier 108 being positioned below a lower surface 134 of the sliding track 102, where the second barrier 108 is not aligned immediately below the first barrier 106. Meanwhile, the first portion 114 and second portion 116 of the table skirt are aligned with the x-axis. In FIG. 1C and FIG. 1D, the first barrier 106 and the second barrier 108 are aligned with the x-axis, with both the first barrier 106 and the second barrier 108 being positioned below a lower surface 134 of the sliding track 102, where the first barrier 106 is aligned with the first portion 114 of the skirt 112 and the second barrier 108 is aligned with the second portion 116 of the skirt 112. However, it should be understood that any other configuration where the skirt 112 is slidable along the sliding track 102 along the x-axis or the z-axis and where the first barrier 106 and the second barrier 108 are slidable along the sliding track 102 along the x-axis or the z-axis and are rotatable about the x-axis, the y-axis, and/or the z-axis are contemplated by the present disclosure.

FIGS. 2-8 show the use of the scatter protection device 100 of the present disclosure in use during any procedure using a radiation emitting device 124 and surrounding an operating table 104. As shown, the perimeter 150 of the sliding track 102 completely surrounds the perimeter 148 of the table 104. However, it should be understood that in some embodiments, the sliding track 102 may not completely surround the perimeter 148 of the table 104. For instance, the sliding track 102 may only align with one, two, or three sides of the table 104, or may only partially align with the entire perimeter 148 of the table 104. In any event, the first barrier 106 and the second barrier 108 can be positioned above an upper surface 126 of the table 104, and the skirt 112, including first portion 114 and second portion 116, can be positioned below a lower surface 128 of the table 104. However, it is also to be understood that one or both of the first barrier 106 and the second barrier 108 can also be positioned below a lower surface 128 of the table 104 if not needed during a particular procedure to shield medical personnel from scatter radiation.

Figure 2:
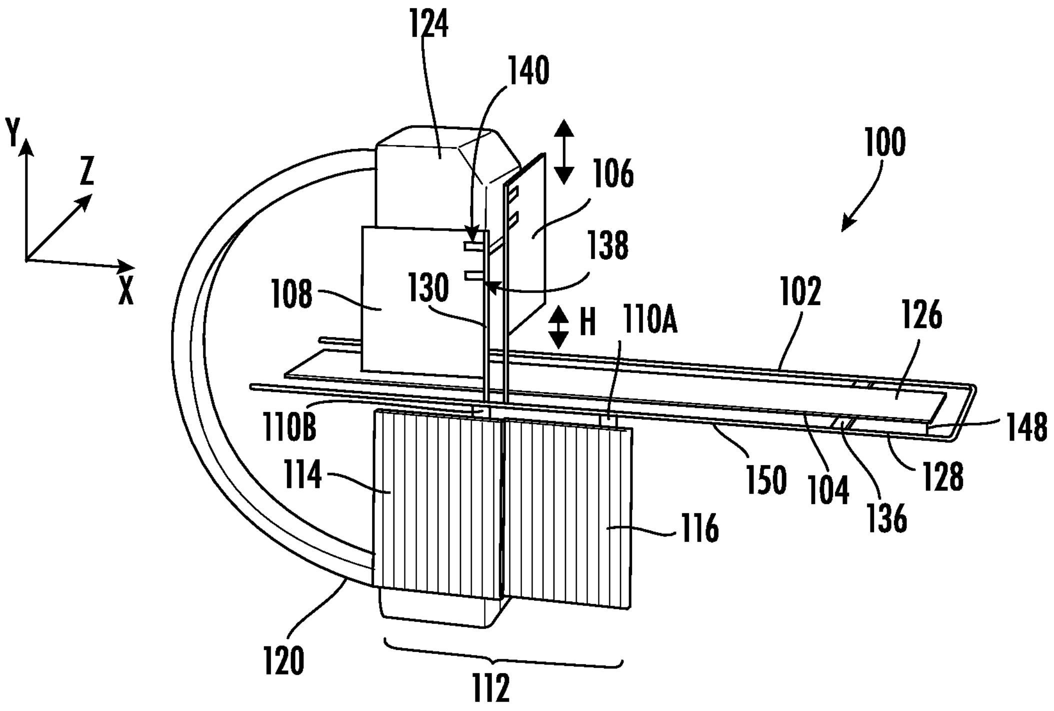
FIG. 2 illustrates a perspective view of one embodiment of the device of the present disclosure when used with an operating table.

Referring to FIG. 2 specifically, the first barrier 106 and the second barrier 108 can be attached to a barrier support 130, where via a hinge 138 and an optional hinge 140. The barrier support 130 can be in the form of a plastic or metal rod, or a rod formed of any other suitable material. The third hinge 138 and the fourth hinge 140 can be locking hinges and can be vertically slidable along the y-axis. For instance, the third hinge 138 and the fourth hinge, 140, if present, can be slidable in the y-direction by a height H. This allows for medical personnel to have access to a precise, customizable location for a particular patient for imaging, diagnosis, treatment, etc. and allows for the device 100 to be utilized for patients of all sizes. The height H can range from about 1 centimeter to about 75 centimeters, such as from about 5 centimeters to about 60 centimeters, such as from about 10 centimeters to about 50 centimeters. In addition, the third hinge 138 and the fourth hinge 140 can be rotatable in along the x-axis to rotate by about 0 degrees to about 180 degrees to position the first barrier 106 and the second barrier 108 in the desired location to allow for access to a portion of a patient's body to be imaged while also protecting medical personnel from scatter radiation. Further, as discussed above, the first hinge 110A and/or the second hinge 1106 allow the first barrier 106 and the second barrier 108 to have additional degrees of freedom of movement so that the first barrier 106 and the second barrier 108 can be rotatable about the x-axis, the y-axis, or the z-axis at the level of the sliding track 102 as well. In addition, an attachment means 136 can be utilized to connect the sliding track 102 to the table 104. The attachment means 136 can be in the form of a clamp, a tie, hook and loop fasteners, or any other suitable attachment means to ensure that the sliding track 102 can be temporarily fixed in position around the perimeter 148 of the table 104.

Figure 3:
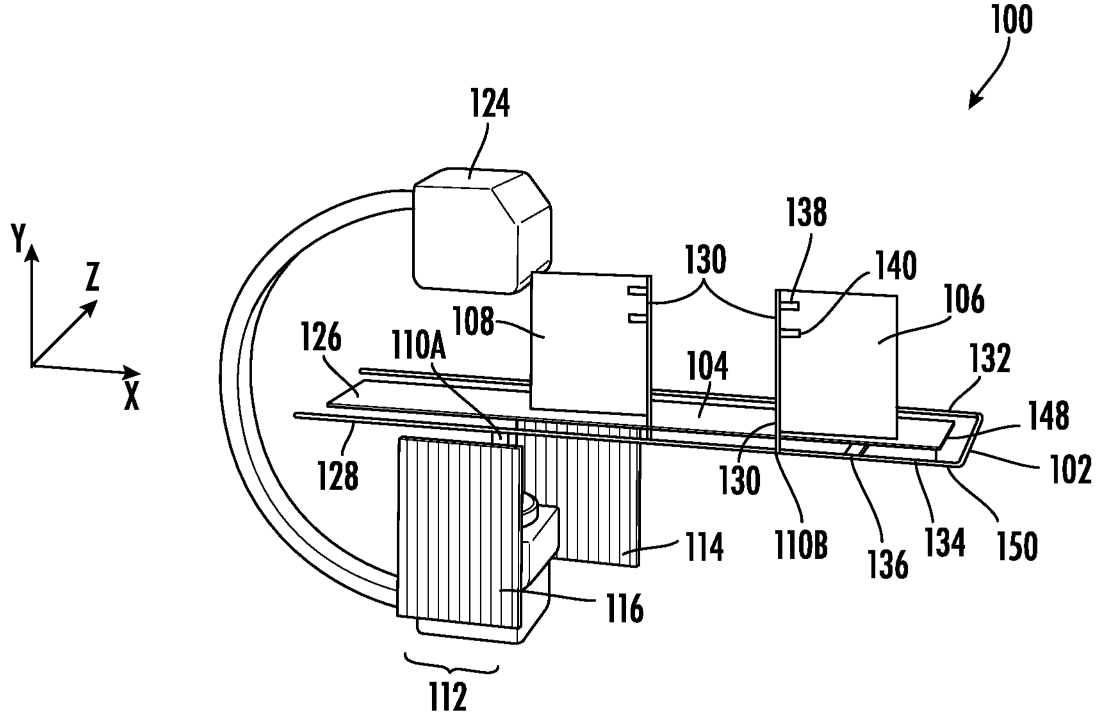
FIG. 3 illustrates another perspective view of one embodiment of the device of the present disclosure when used with an operating table.

Referring now to FIG. 3, another possible configuration for the scatter radiation device 100 of the present disclosure is shown, where the first portion 114 and the second portion 116 of the skirt 112 are positioned on opposite sides of the sliding track 102, where such an arrangement can protect medical personnel standing on opposite sides of the table 104 along the x-axis. In addition, the first barrier 106 and the second barrier 108 are spaced apart from each other along the x-axis. Again, such a configuration can allow access to an area of a patient to be imaged, diagnosed, or treated, while protecting one or more medical personnel nearby.

Figure 4:
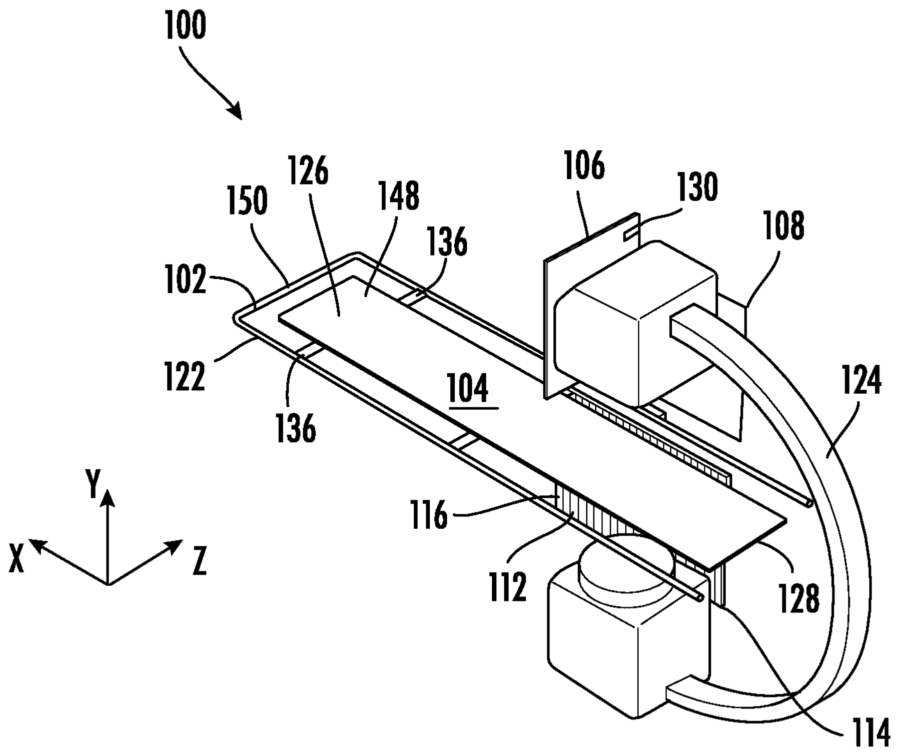
FIG. 4 illustrates still another perspective view of one embodiment of the device of the present disclosure when used with an operating table.

Referring now to FIG. 4, another possible configuration for the scatter radiation device 100 of the present disclosure is shown, where the first portion 114 and the second portion 116 of the skirt 112 are positioned adjacent each other along the same side of the sliding track 102, where such an arrangement can protect medical personnel standing near the table 104 along the x-axis. In addition, the first barrier 106 can be rotated via hinge 110 (not shown) along the z-axis while the second barrier 108 can be positioned along the x-axis. Such a configuration can allow access to an area of a patient to be imaged, diagnosed, or treated, while protecting one or more medical personnel nearby.

Figure 5:
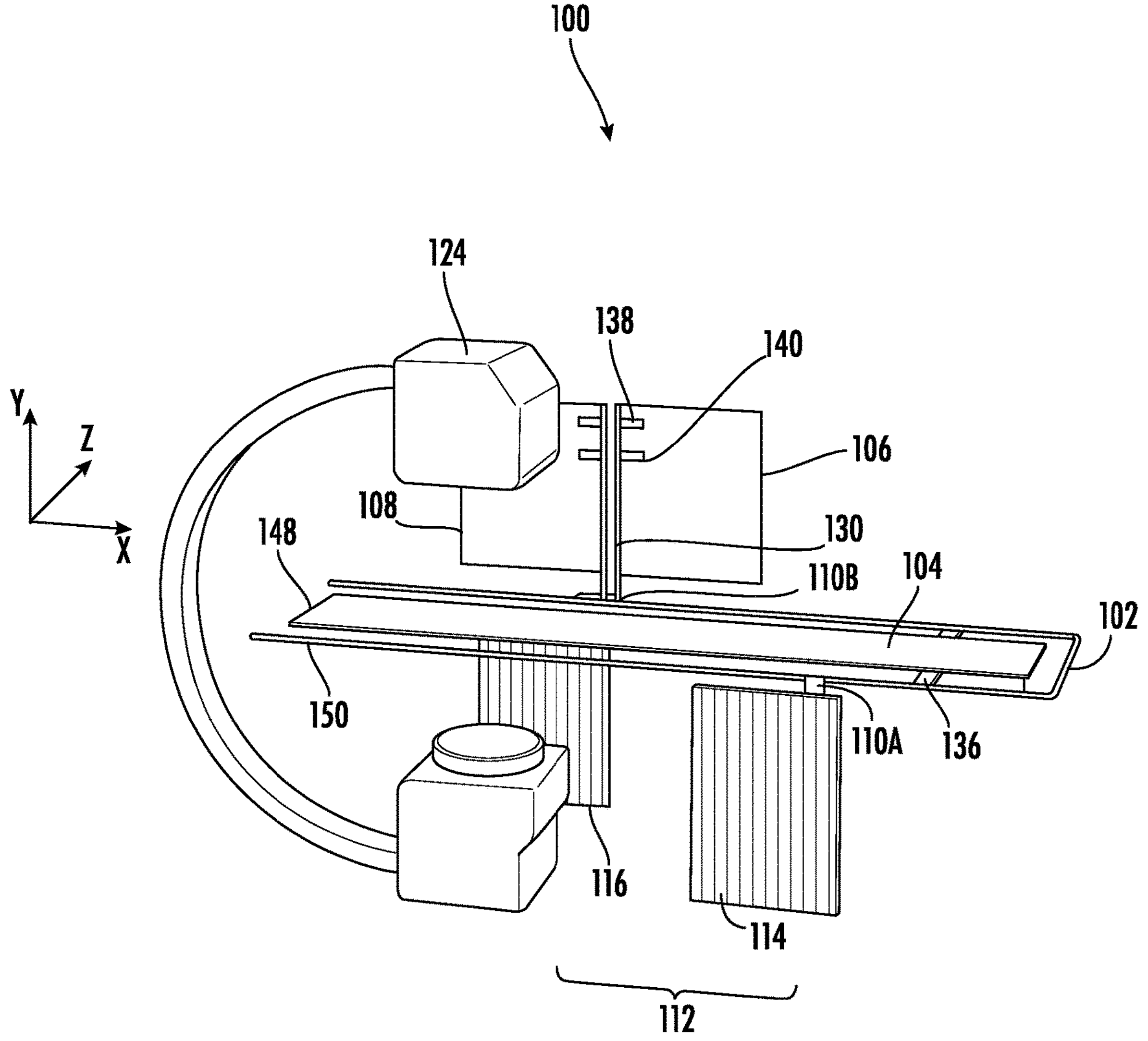
FIG. 5 illustrates yet another perspective view one embodiment of the device of the present disclosure when used with an operating table.

Turning now to FIG. 5, another possible configuration for the scatter radiation device 100 of the present disclosure is shown, where the first portion 114 and the second portion 116 of the skirt 112 are positioned on opposite sides of the sliding track 102 and are also spaced apart from each other along the x-axis rather than being directly opposite each other, where such an arrangement can protect medical personnel standing on opposite sides of the table 104 at different positions along the x-axis. In addition, the first barrier 106 and the second barrier 108 can be placed adjacent each other along the x-axis. Again, such a configuration can allow access to an area of a patient to be imaged, diagnosed, or treated, while protecting one or more medical personnel nearby.

Figure 6:
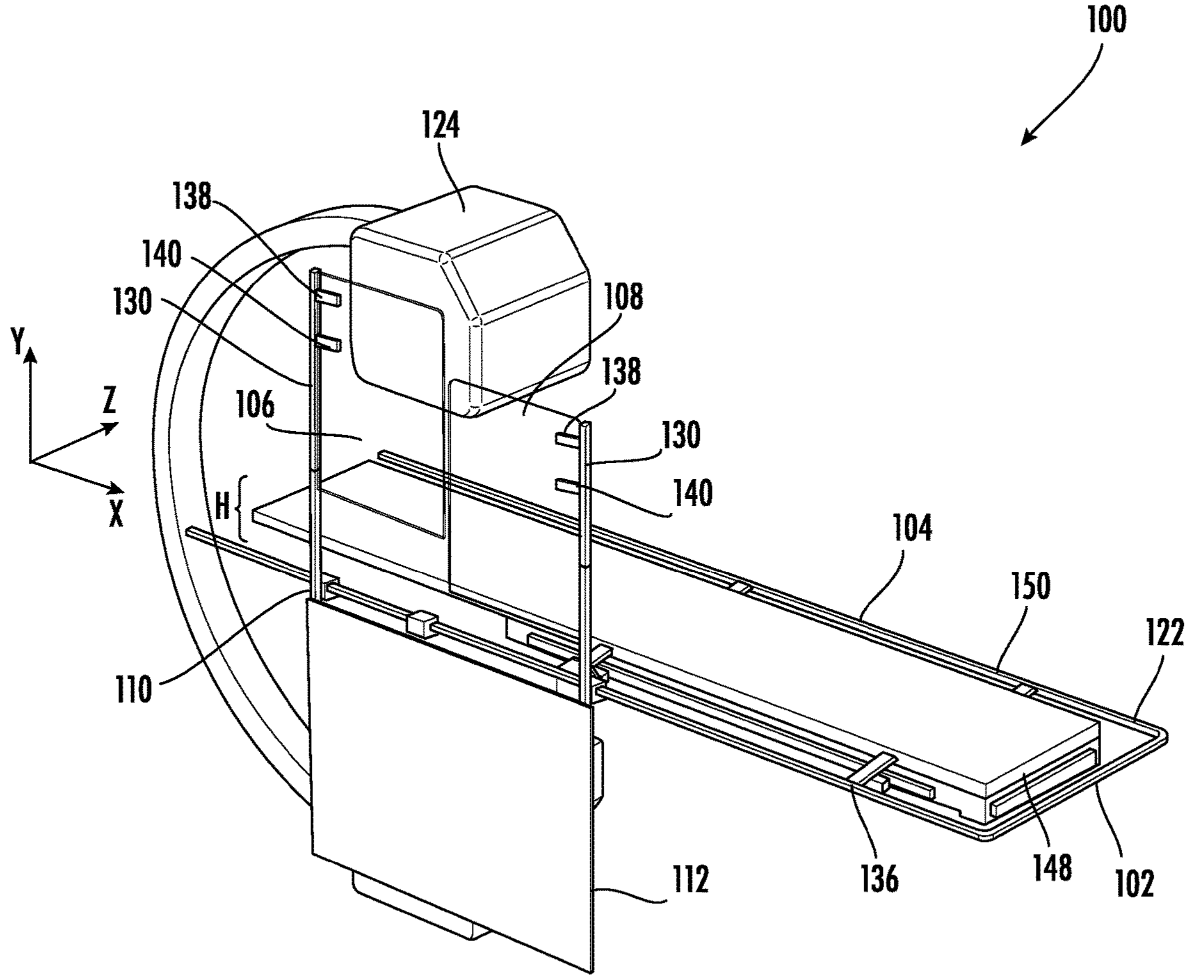
FIG. 6 illustrates one more perspective view of one embodiment of the device of the present disclosure when used with an operating table.

In FIG. 6, another possible configuration for the scatter radiation device 100 of the present disclosure is shown, where the first portion 114 and the second portion 116 of the skirt 112 are positioned adjacent each other in the x-axis along the sliding track 102, where such an arrangement can protect medical personnel standing on the same side of the table 104 and next to each other along the x-axis. In addition, the first barrier 106 and the second barrier 108 can be placed adjacent each other along the x-axis. As shown, the first barrier 106 can be moved vertically along the y-axis via support 130 and/or a third hinge 138 and/or a fourth hinge 140 by a height H to provide access to a particular area of a patient to be imaged, diagnosed, and/or treated. Again, such a configuration can allow access to an area of a patient to be imaged, diagnosed, or treated, while protecting one or more medical personnel nearby.

Figure 7:
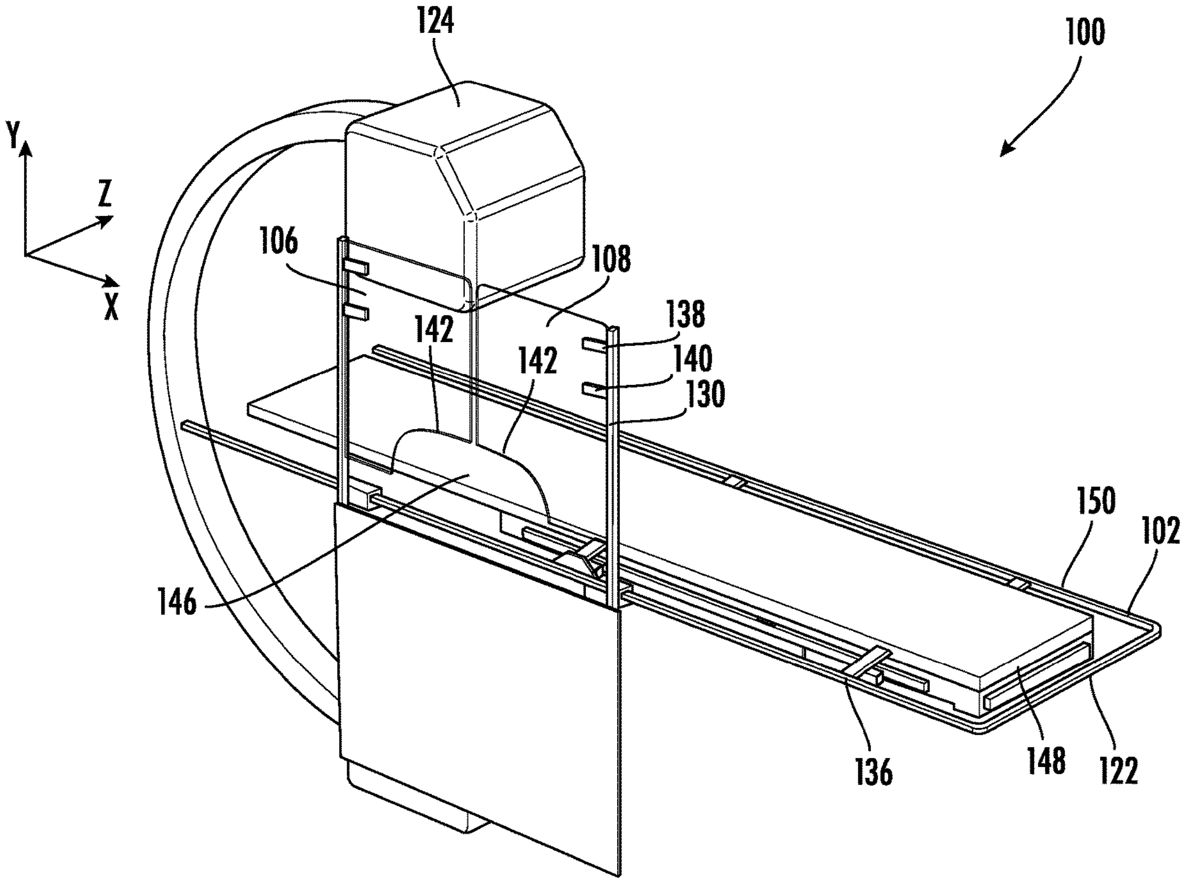
FIG. 7 illustrates a perspective view of an additional embodiment of the device of the present disclosure when used with an operating table.
Figure 8:
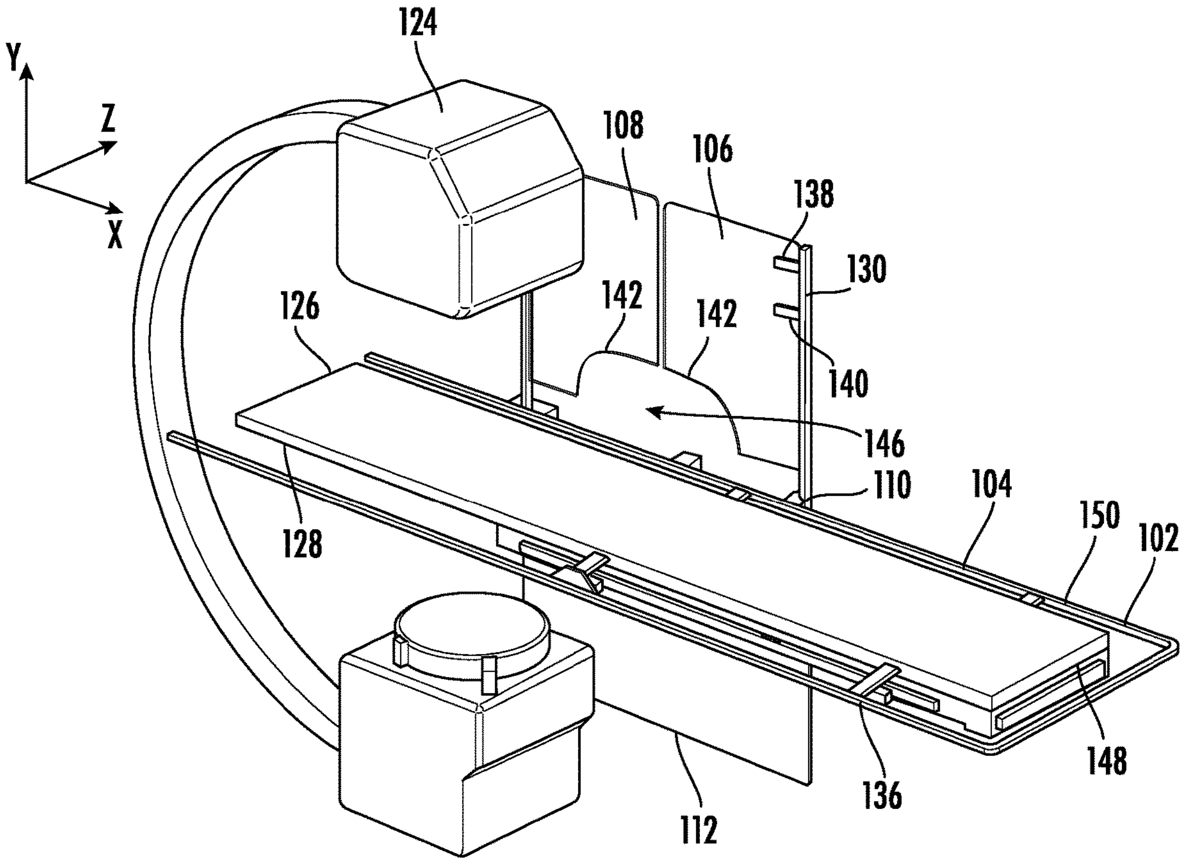
FIG. 8 illustrates another perspective view of an additional embodiment of the device of the present disclosure when used with an operating table.

Meanwhile, in FIGS. 7 and 8, another possible configuration for the scatter radiation device 100 of the present disclosure is shown, where the first portion 114 and the second portion 116 of the skirt 112 are positioned adjacent each other in the x-axis along the sliding track 102, where such an arrangement can protect medical personnel standing on the same side of the table 104 and next to each other along the x-axis. In addition, the first barrier 106 and the second barrier 108 can be placed adjacent each other along the x-axis. As shown, the first barrier 106 and/or the second barrier 108 can have corresponding cutout sections 142 that each define an opening 146 to provide access to a particular area of a patient to be imaged, diagnosed, and/or treated. Such features allow for medical personnel to insert their hands underneath the barriers and allow for medical personnel to have better access to the area of the patient's body to be imaged while protecting medical personnel at the same time.

The following example serves to illustrate the effectiveness of the device of the present disclosure.

It should be understood that the term lead equivalence means the thickness of lead affording the same attenuation, under specified conditions, as the material in question (e.g., the acrylic or glass barriers of the present disclosure).

EXAMPLE

Figure 9:
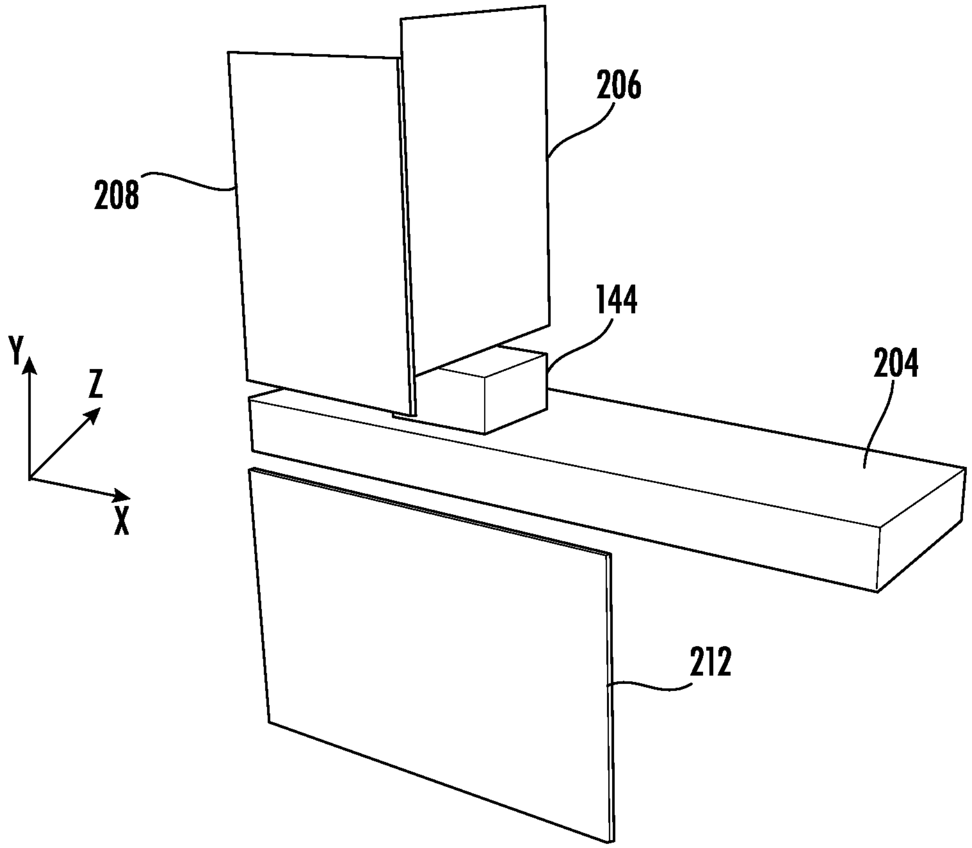
FIG. 9 illustrates a visualization of simulation geometry utilized to determine the effectiveness of the device of the present invention to protect medical personal from exposure to scatter radiation when imaging a patient's tissue.

In this Example, a simulation utilizing Monte Carlo N-Particle Transport Code (MCNP), a software package for simulating nuclear processes developed by Los Alamos National Labs, was conducted utilizing geometries corresponding to the scatter protection device of the present disclosure to verify the effectiveness of the scatter protection device at preventing scatter radiation exposure. FIG. 9 illustrates a visualization of the simulation geometry utilized to determine the effectiveness of the device of the present invention to protect medical personnel from exposure to scatter radiation when imaging a patient's tissue 144. Block 204 represents an operating table, block 206 represents the first barrier, block 208 represents the second barrier, and block 212 represents the skirt. Block 206 and block 208 were simulated using a 1.6 mmPb equivalent glass, and block 212 was simulated using a 1 mmPb equivalent apron.

To determine percent radiation attenuation accomplished, the glass and apron were placed directly in front of an X-ray beam at 100 kVp, and tube current varied from 1 milliamp (mA) to 5 mA. After an ion chamber placed behind the glass and apron detected radiation, radiation emitted without the glass and apron was also recorded. With these comparisons, the glass decreased exposure by 99.978% and the apron decreased exposure by 87.77%.

Figure 10:
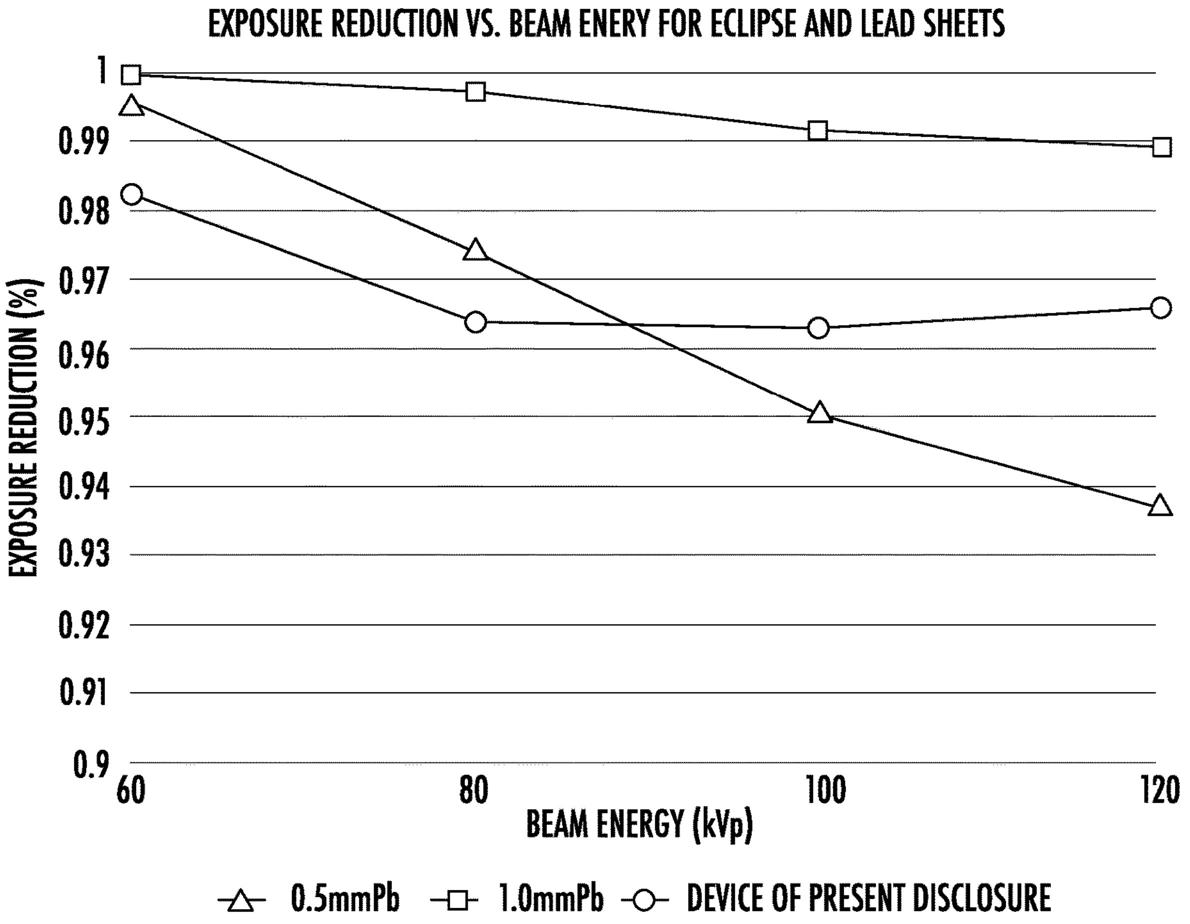
FIG. 10 is a graph illustrating the reduction in exposure to scatter radiation based on the simulation shown in FIG. 9 as compared to lead barriers of varying lead equivalence.

Following testing of the physical materials selected described above, simulations were used to test the efficacy of the scatter radiation protection device in use. Simulations included the operating table as block 202, a tissue-equivalent slab representing the patient as block 144, the cone-shaped X-ray beam source, and a tally representing the clinician. The simulated device, clinician, and X-ray beam were placed to simulate a cardiac catheterization procedure. In simulations featuring the device, the simulation showed more than 95% reduction in scatter exposure to the clinician below the table, represented by block 202, as shown in FIG. 10.

Based on the simulation results, it is shown that the geometry of the device of the present disclosure produces a reduction in scatter radiation exposure underneath the table consistently exceeding 95%. Although the exposure reduction does not quite reach the required 1 mm Pb equivalence specified in the design inputs, this is hypothesized to be due to the differences in data collection between the simulation and the material testing results. This is evidenced by the results of material testing conducted—the 1 mm Pb-equivalent PPE only blocked 87.77% of the 100 kVp X-rays incident on it. However, it was determined that this apron was defective, which affected these results. Nonetheless, the geometry of the device is considered to fully meet the specification.

While the present disclosure has been described with reference to certain exemplary embodiments thereof, those skilled in the art may make various modifications to the described embodiments of the present disclosure without departing from the scope of the disclosure. The terms and descriptions used herein are set forth by way of illustration only and not meant as limitations. In particular, although the present disclosure has been described by way of examples, a variety of compositions and processes would practice the inventive concepts described herein. Although the disclosure has been described and disclosed in various terms and certain embodiments, the scope of the disclosure is not intended to be, nor should it be deemed to be, limited thereby and such other modifications or embodiments as may be suggested by the teachings herein are particularly reserved, especially as they fall within the breadth and scope of the claims here appended. Those skilled in the art will recognize that these and other variations are possible within the scope of the disclosure as defined in the following claims and their equivalents.

What is claimed is:

1. A scatter radiation protection device comprising:

a barrier, wherein the barrier is movable in an x-direction, a y-direction, and a z direction;

a skirt, wherein the skirt is movable in an x-direction; and a sliding track having an upper surface and a lower surface, wherein the barrier and the skirt are configured for connection to the sliding track, wherein the barrier and the skirt each provide for at least 0.5 millimeters of lead (mmPb) equivalence, wherein the barrier and the skirt are connected to the sliding track via a hinge.

2. The scatter radiation protection device of claim 1, wherein the barrier includes a first barrier and a second barrier.

3. The scatter radiation protection device of claim 1, wherein the barrier includes a cutout section to define an opening.

4. The scatter radiation protection device of claim 1, wherein the skirt includes a first portion and a second portion.

5. The scatter radiation protection device of claim 1, wherein the barrier comprises a transparent or translucent material.

6. The scatter radiation protection device of claim 5, wherein the barrier comprises leaded glass or leaded acrylic.

7. The scatter radiation protection device of claim 1, wherein the skirt includes lead.

8. The scatter radiation protection device of claim 1, wherein the skirt is further movable in the y-direction.

9. The scatter radiation protection device of claim 1, wherein the sliding track defines a groove around a perimeter of the sliding track.

10. The scatter radiation protection device of claim 9, wherein the groove is located on an upper surface of the sliding track.

11. The scatter radiation protection device of claim 1, wherein the hinge is slidable, rotatable, or a combination thereof.

12. The scatter radiation protection device of claim 1, further comprising a barrier support, wherein the barrier is connected to the barrier support via an additional hinge.

13. The scatter radiation protection device of claim 12, wherein the additional hinge is slidable, rotatable, or a combination thereof.

14. The scatter radiation protection device of claim 13, wherein the barrier is slidable in the y-direction by a height H via the additional hinge.

15. The scatter radiation protection device of claim 14, wherein the height H ranges from about 1 centimeter to about 75 centimeters.

16. The scatter radiation protection device of claim 1, further comprising an attachment means configured to connect the scatter radiation protection device to a table.

17. The scatter radiation protection device of claim 16, wherein the barrier is slidable around an entire perimeter of the table.

18. The scatter radiation protection device of claim 16, wherein the skirt is slidable around an entire perimeter of the table.

19. The scatter radiation protection device of claim 1, wherein the scatter radiation protection device exhibits greater than 95% reduction in scatter radiation exposure compared to when the scatter radiation protection device is not used.

* * * * *